(12) United States Patent
Serna

(10) Patent No.: US 9,278,025 B1
(45) Date of Patent: Mar. 8, 2016

(54) HANDHELD CONTACT APPLICATOR SYSTEMS

(71) Applicant: Robert Serna, Redondo Beach, CA (US)

(72) Inventor: Robert Serna, Redondo Beach, CA (US)

( * ) Notice: Subject to any disclaimer, the term of this patent is extended or adjusted under 35 U.S.C. 154(b) by 0 days.

(21) Appl. No.: 14/531,924

(22) Filed: Nov. 3, 2014

Related U.S. Application Data

(60) Provisional application No. 61/899,273, filed on Nov. 3, 2013.

(51) Int. Cl.
*A61F 9/00* (2006.01)

(52) U.S. Cl.
CPC .................... *A61F 9/0061* (2013.01)

(58) Field of Classification Search
CPC .................................................. A61F 9/0061
USPC ........................................................ 294/1.2
See application file for complete search history.

(56) References Cited

U.S. PATENT DOCUMENTS

| | | | | |
|---|---|---|---|---|
| 2,924,481 A | * | 2/1960 | Wagstaff | 81/53.11 |
| 3,424,486 A | * | 1/1969 | Corley | 294/1.2 |
| 3,645,576 A | * | 2/1972 | Horres | 294/1.2 |
| 4,026,591 A | | 5/1977 | Cleaveland | |
| 4,037,866 A | * | 7/1977 | Price | 294/1.2 |
| 4,093,291 A | | 6/1978 | Schurgin | |
| 4,326,742 A | * | 4/1982 | Ingram | 294/1.2 |
| 4,378,126 A | | 3/1983 | Procenko | |
| 4,565,396 A | | 1/1986 | Larimer | |
| 5,050,918 A | * | 9/1991 | Kolze | 294/1.2 |
| 5,558,374 A | * | 9/1996 | Harrison | 294/1.2 |

* cited by examiner

*Primary Examiner* — Dean Kramer
(74) *Attorney, Agent, or Firm* — RG Patent Consulting, LLC; Rachel Gilboy

(57) ABSTRACT

A handheld contact applicator system comprising a handheld contact applicator assembly having a handle body having a proximate end, a distal end, an aperture, and a length, an inserter/remover assembly having a shaft, a release button, and a contact engager; wherein the handheld contact applicator system comprises the handheld contact applicator assembly. The handheld contact applicator assembly comprises the handle body and the inserter/remover assembly in cooperative and functional combination.

15 Claims, 5 Drawing Sheets

HANDHELD CONTACT APPLICATOR SYSTEMS

CROSS-REFERENCE TO RELATED APPLICATION

The present application is related to and claims priority from prior provisional application Ser. No. 61/899,273, filed Nov. 3, 2013 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

The following includes information that may be useful in understanding the present invention(s). It is not an admission that any of the information provided herein is prior art, or material, to the presently described or claimed inventions, or that any publication or document that is specifically or implicitly referenced is prior art.

BACKGROUND OF THE INVENTION

1. Field of the Invention

The present invention relates generally to the field of insertion and removal devices and more specifically relates to a handheld contact applicator specifically designed for the insertion and removal of contact lenses to provide contact lens wearers a simple and sanitary means of handling their lenses.

2. Description of the Related Art

Millions of Americans suffer from problems related to their vision. Whether one has a classic case of Myopia (near-sightedness), Hyperopia (farsightedness), Astigmatism (distorted vision), Presbyopia (the need for bifocals) or more than one of the above, not being able to see clearly can effect virtually every aspect of a person's life. Most people correct their vision by wearing eye glasses or contact lenses. In particular, contact lenses are an extremely popular solution to the problems associated with poor vision. Contacts are so popular in fact, that nearly 24 million Americans wear them. According to statistics compiled by the University of Michigan, Kellogg Eye Center, of these 24 million, nearly 75% opt for soft lenses, while others choose to wear hard, rigid gas permeable or extended wear contacts. Regardless of the variety of contacts an individual chooses to wear, a consistent regimen of care must be taken in order to ensure the optimal health of the eye. Contact lenses are tiny, curved plastic discs, which are designed to be placed directly over the cornea and are held in place by a thin film of tears, as well as by surface tension (capillary action.)

Traditionally, most people insert their contact lenses one at a time, by placing each lens on the tip of the index finger and directly setting it over the cornea. While a fresh, clean pair of contact lenses can vastly improve one's vision, a pair that is soiled can potentially damage one's eyesight. When lenses are not cleaned and handled properly, dirt, oil and bacteria are directly deposited into the eye, via the contact. Resulting in everything from irritation, a scratched cornea, eye infections and blurred vision, wearing a pair of contaminated contact lenses can result in permanent intolerance to contacts, and in some extreme cases can even cause blindness.

While most conscientious contact lens wearers wash their hands before inserting their contact lenses, many others do not. Overlooking the importance of freshly washed hands, many contact lens wearers simply do not realize the dangerous consequences of handling contacts and perhaps most importantly, touching the eye, with unclean hands. Additionally, many contact lens wearers experience difficulty inserting and removing their lenses. Because of their very size and shape, properly inserting or removing a contact lens can be a daunting task, especially considering that most contact lens wearers cannot see clearly during this process. A sanitary and convenient means for insertion and/or removal of contacts into eyes is desirable.

Various attempts have been made to solve the above-mentioned problems such as those found in U.S. Pat. No. 4,378,126 to Leonid Procenko; U.S. Pat. No. 4,093,291 to Herbert L. Schurgin; U.S. Pat. No. 4,026,591 to John A. Cleaveland; and U.S. Pat. No. 4,565,396 to John M. Larimer. This prior art is representative of contact lens accessories. None of the above inventions and patents, taken either singly or in combination, is seen to describe the invention as claimed.

Ideally, a handheld applicator specifically designed for the insertion and removal of contact lenses will provide contact lens wearers with a simple and sanitary means of handling their lenses and, yet would operate reliably and be manufactured at a modest expense. Thus, a need exists for a reliable handheld contact applicator system to avoid the above-mentioned problems.

BRIEF SUMMARY OF THE INVENTION

In view of the foregoing disadvantages inherent in the known contact accessories art, the present invention provides a novel handheld contact applicator. The general purpose of the present invention, which will be described subsequently in greater detail is to provide a safe and efficient means for inserting and removing contact lens from eye(s).

A handheld contact applicator system is disclosed herein, in a preferred embodiment, comprising: a handheld contact applicator assembly having a handle body (having a proximate end, a distal end, an aperture, and a length), an inserter/remover assembly (having a shaft, a release button, and a contact engager); wherein the handheld contact applicator system comprises the handheld contact applicator assembly. The handheld contact applicator assembly comprises the handle body and the inserter/remover assembly in cooperative and functional combination.

The handle body comprises the proximate end, the distal end, the aperture, and the length, as mentioned; wherein the parameters of the handle body are defined by the proximate end, and the distal end having the length thereby defined; the aperture passes through the handle body.

The inserter/remover assembly comprises the shaft, the release button, and the contact engager; wherein the contact engager is preferably flexible to avoid contact-injury to the eye. The contact engager is normally concave-tensioned, wherein the contact engager engages a contact lens via surface tension (capillary action) for insertion. In a similar but reverse manner the contact engager disengages the contact lens via breaking capillary action for removal via flexing the contact engager to a convex positioning temporarily (other means of removal may be employed).

In preferred embodiments the handheld contact applicator assembly comprises plastic or rubberized material or the like (other suitable equivalents may be used). The plastic, when used, is soft to prevent eye injury and also able to be sterilized to prevent harboring of bacteria and the like.

Relationally speaking, the inserter/remover assembly is nearest the proximate end of the handle body. The inserter/remover assembly is in mechanical communication with the handle body; the shaft passing through the aperture perpendicular to the handle body, the release button located on a terminal end of the shaft and the contact engager located opposing the release button on a leading end of the shaft, The release button is manually activated when depressed, to facilitate release for insertion and alternately to couple to for removal, the contact lens touch-coupled to the contact engager. As such, the handheld contact applicator assembly is structured and arranged to facilitate the insertion and the removal of the contact lens in a remote capacity in order to effectively eliminate finger to eye contact. The handheld contact applicator is also able to be used as a hygienic means of adjusting the contact lens which have slipped off a cornea.

It should be appreciated that when referring to the handheld contact applicator system disclosed herein that the contact lens is selected from the group consisting of soft-lens, hard-lens, gas-permeable-lens, and extended-wear-lens. This list is exemplary and is not intended to be limiting in any way.

A method of using a handheld contact applicator system is also disclosed herein comprising the steps of: adhering a contact lens to a contact engager of a handheld contact applicator assembly (via surface tension—using liquid or the like), placing the contact lens onto an eye surface, and pressing a release button to release the contact lens and couple the contact lens onto the eye surface for wear. Thus remote insertion may occur without direct use of a finger. The method may further comprise the step of removing the contact lens from the eye surface when wearing is completed, also without direct use of at least one finger adjacent the eye surface.

The present invention holds significant improvements and serves as a handheld contact applicator system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, handheld contact applicator system, constructed and operative according to the teachings of the present invention.

The various embodiments of the present invention will hereinafter be described in conjunction with the appended drawings, wherein like designations denote like elements.

DETAILED DESCRIPTION

Figure 1:
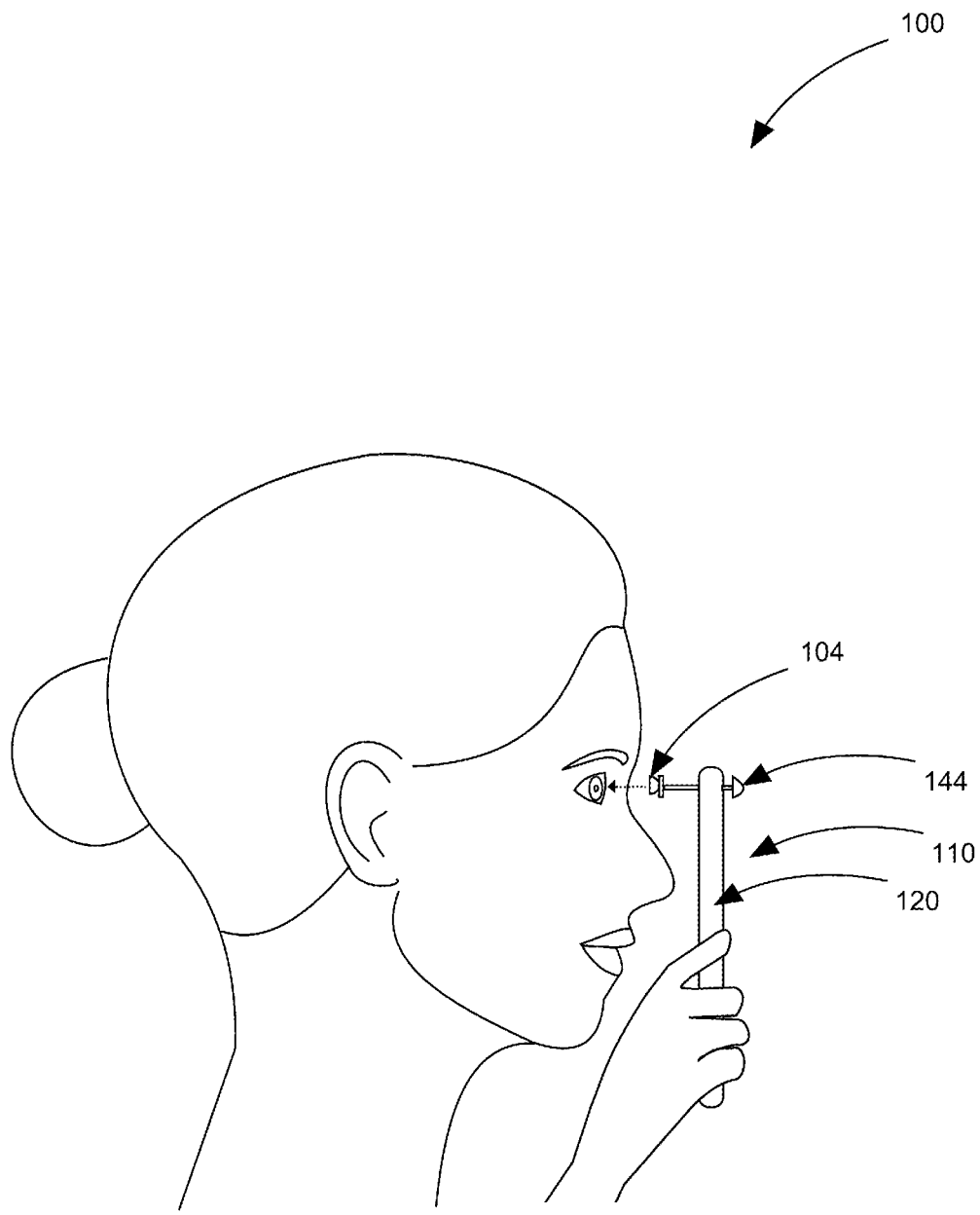
FIG. 1 shows a perspective view illustrating a handheld contact applicator assembly of the handheld contact applicator system in an in-use condition (inserting a contact) according to an embodiment of the present invention.

As discussed above, embodiments of the present invention relate to a contacts accessory and more particularly to a handheld contact applicator as used to improve the efficiency, hygiene, and safety of contact insertion and removal.

Generally speaking, the handheld contact applicator comprises a specially designed handheld mechanism comprised of an elongated, ergonomically shaped handle, at the top of which is a circular shaped cup-like lens holder (contact engager) preferably manufactured of soft and flexible rubber material.

This disc-like cup may be designed to easily hold virtually any standard soft, hard, or rigid gas permeable lens. The elongated shaft of the handheld contact applicator may be sized and shaped appropriately to effectively ensure a comfortable grip. Manufactured of lightweight plastic or comparable material, the handheld contact applicator handle may measure approximately 7 inches in total length and ½ inch in width. The actual flexible rubber contact lens cup holder may be a concave circle measuring between ¼-⅝ of an inch in diameter. Positioned at the proximate end of this handle may be a simple release lever, configured in the form of an easily depressed button which is internally connected to the actual contact lens suction cup, gently releasing or removing the inserted contact lens via a simple spring or comparable mechanism which secures the cup to the shaft.

Use of the handheld contact applicator may be relatively simple and straight forward. After washing the hands, the user may comfortably grasp the handheld contact applicator in hand. The user may then open their contact lens case, retrieving the contact lens by hand and placing it directly onto the circular shaped disc-like suction cup, located at the top of the unit. Alternately, the contact lens wearer could use the handheld contact applicator to actually lift their lens out of the case, by using the rubber contact lens holder as a scoop on which to retrieve the lens. The user may then position the handheld contact applicator so that the contact lens was positioned directly over the cornea. The user may then simply depress the integrated release handle located at the base of the unit shaft, gently releasing the contact lens directly onto the eye (surface.)

This process may then be repeated with the remaining contact. After wear, the user may remove their contact lenses by once again utilizing the handheld contact applicator. Positioning the lens holder in front of the handheld contact applicator, the user may lightly touch the cup to their contact, thus gently pulling the contact from the eye. The user could then drop the contact lens into its storage case, utilizing the unit to remove their second lens. The user may then simply rinse the cup holder clean and store the unit alongside their other eye care accessories.

There are many significant benefits and advantages associated with the handheld contact applicator. Foremost, the handheld contact applicator may offer consumers a hygienic means of handling their contact lenses. Providing a safe and effective means of inserting and removing contact lenses, consumers should appreciate that the handheld contact applicator may offer a sanitary alternative to touching contact lenses with one's fingers or hands. Additionally, because use of the product may eliminate the need to directly touch the eye, the handheld contact applicator could greatly reduce the potential for eye infections and vision problems that are associated when germs and bacteria are deposited into the eyes via transfer from the hands.

Easy to use, the handheld contact applicator may aid in inserting contact lenses, in a few, simple steps. This benefit should prove especially advantageous to teens who are wearing contacts for the first time and who might find it difficult to insert or remove their lenses. Further, consumers who suffer various maladies such as arthritis and other medical conditions that can compromise their manual dexterity should greatly appreciate the ease of which the handheld contact applicator may enable them to insert and remove their contacts. Consumers should also appreciate that the handheld contact applicator may be used with virtually any contact lens. Safe for soft, hard, gas permeable and extended wear lenses, the handheld contact applicator is able to be used by the majority of contact lens wearers. Another advantage is found in the unique design of the unit. Although specially intended to insert contact lenses, the unique, soft disc of the handheld contact applicator may also be used as a hygienic means of adjusting contact lenses which have slipped off the cornea or shifted out of place in the eye.

The handheld contact applicator is a practical product invention which provides contact lens wearers a sanitary method of inserting and removing their contacts. Simple to use, this innovative product may prove an invaluable tool in the care of contact lenses, resulting in clear vision and healthy eyes.

Figure 2:
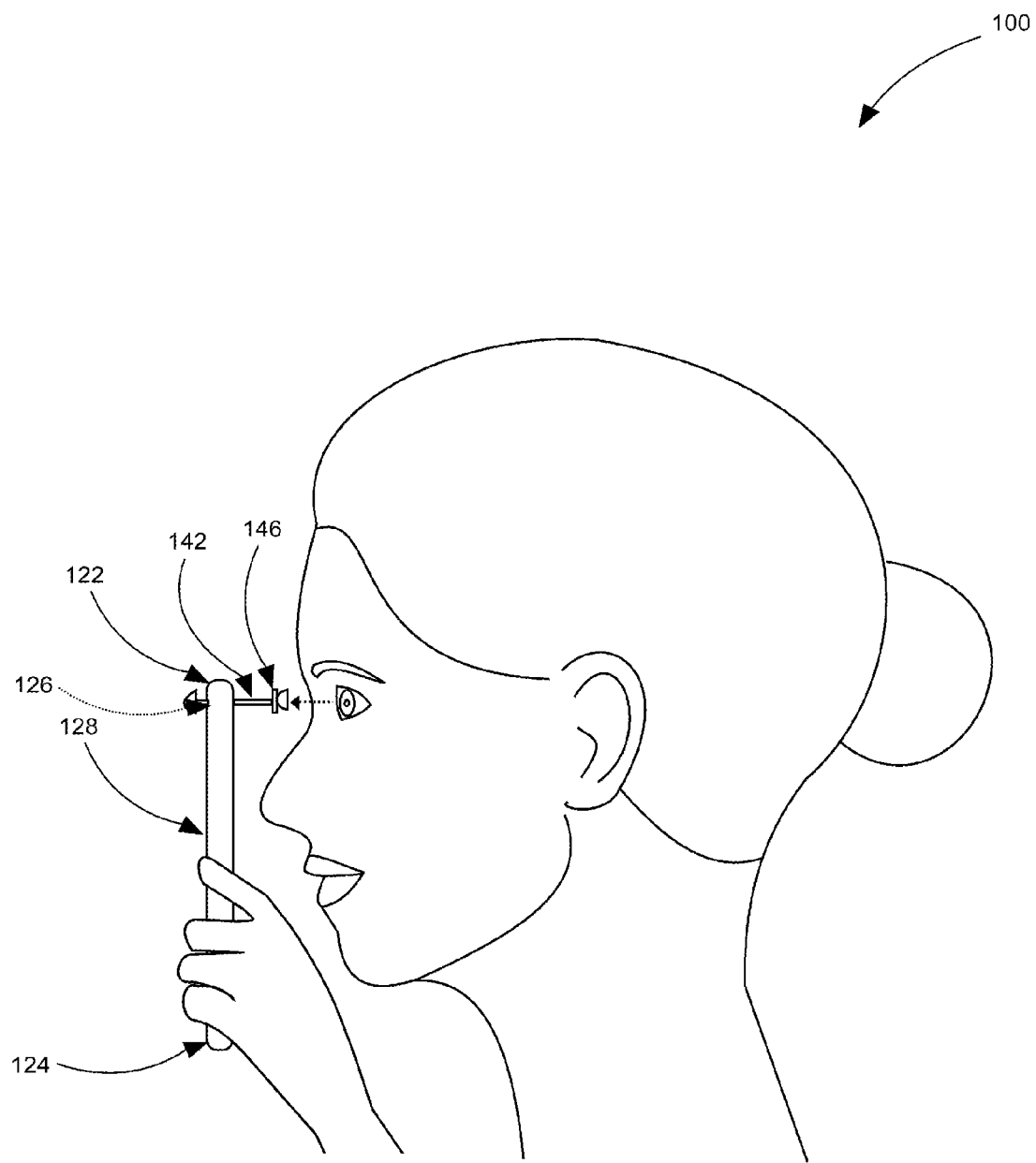
FIG. 2 is a perspective view illustrating the handheld contact applicator assembly of the handheld contact applicator system in an in-use condition (removing a contact) according to an embodiment of the present invention of FIG. 1.

Referring now more specifically to the drawings by numerals of reference there is shown in FIGS. 1 and 2, perspective views illustrating handheld contact applicator assembly 110 of handheld contact applicator system 100 in in-use condition(s) (inserting contact lens 104 and removing contact lens 104, respectively) according to an embodiment of the present invention.

Handheld contact applicator system 100 comprises: handheld contact applicator assembly 110 having handle body 120 (having proximate end 122, distal end 124, aperture 126, and a length 128), inserter/remover assembly 140 (having shaft 142, release button 144, and contact engager 146; wherein handheld contact applicator system 100 comprises handheld contact applicator assembly 110.

Handheld contact applicator assembly 110, as shown, comprises handle body 120 and inserter/remover assembly 140 in cooperative and functional combination; wherein handle body 120 comprises proximate end 122, distal end 124, aperture 126, and the length 128. As such, the parameters of handle body 120 are defined by proximate end 122, and distal end 124 having the length 128 thereby defined. Aperture 126 passes through handle body 120, wherein shaft 142 is perpendicular to handle body 120 for ease of use.

Inserter/remover assembly 110 comprises shaft 142, release button 144, and contact engager 146; wherein inserter/remover assembly 110 is in mechanical communication with handle body 120; shaft 142 passing through aperture 126 perpendicular to handle body 120; release button 144 located on terminal end 150 of shaft 142 (not adjacent the eye when used) and contact engager 146 located opposing release button 144 on leading end 152 of the shaft 142 (adjacent the eye when is use, as shown in FIG. 1.)

Release button 144 is able to be manually activated when depressed, to facilitate release for insertion (FIG. 1) and alternately to couple to for removal (FIG. 2), contact lens 104 as touch-coupled to contact engager 146; as such handheld contact applicator assembly 110 of handheld contact applicator system 100 is structured and arranged to facilitate insertion and removal of the contact lens 104 (respectively) in a remote capacity in order to effectively eliminate finger to eye contact. Release button 144 may be spring-tensioned; spring tensioning means held within parameters of handle body 120. Shaft 142 preferably comprises a tubular rod which is semi-rigid.

Figure 3:
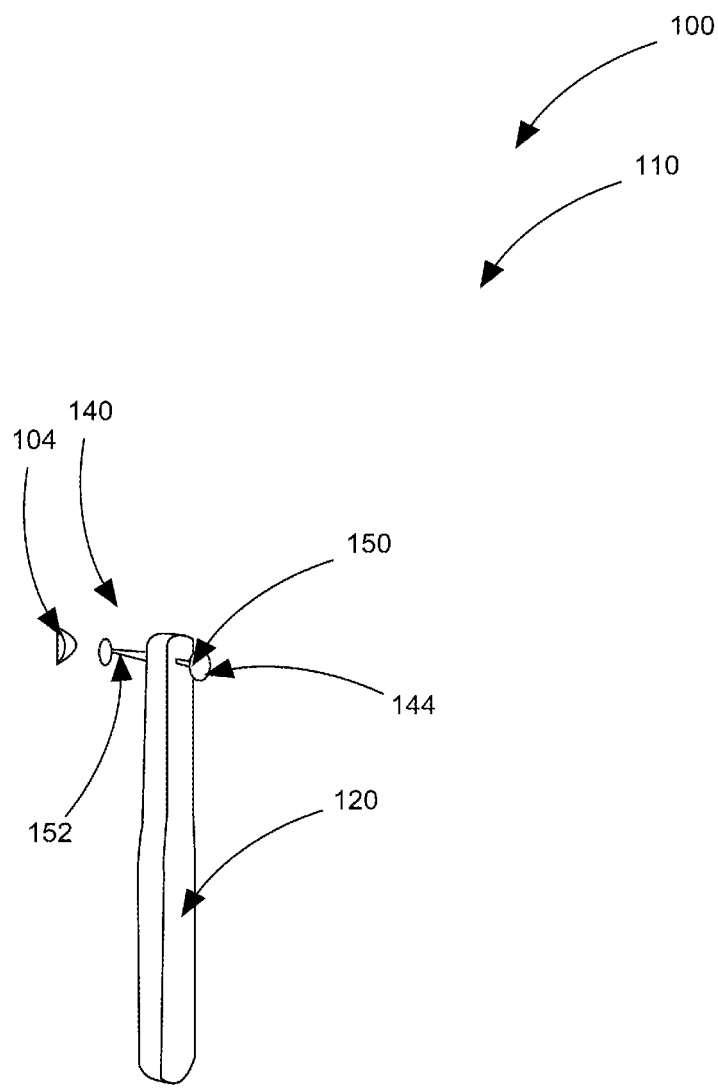
FIG. 3 is a perspective view illustrating the handheld contact applicator assembly according to an embodiment of the present invention of FIG. 1.
Figure 4:
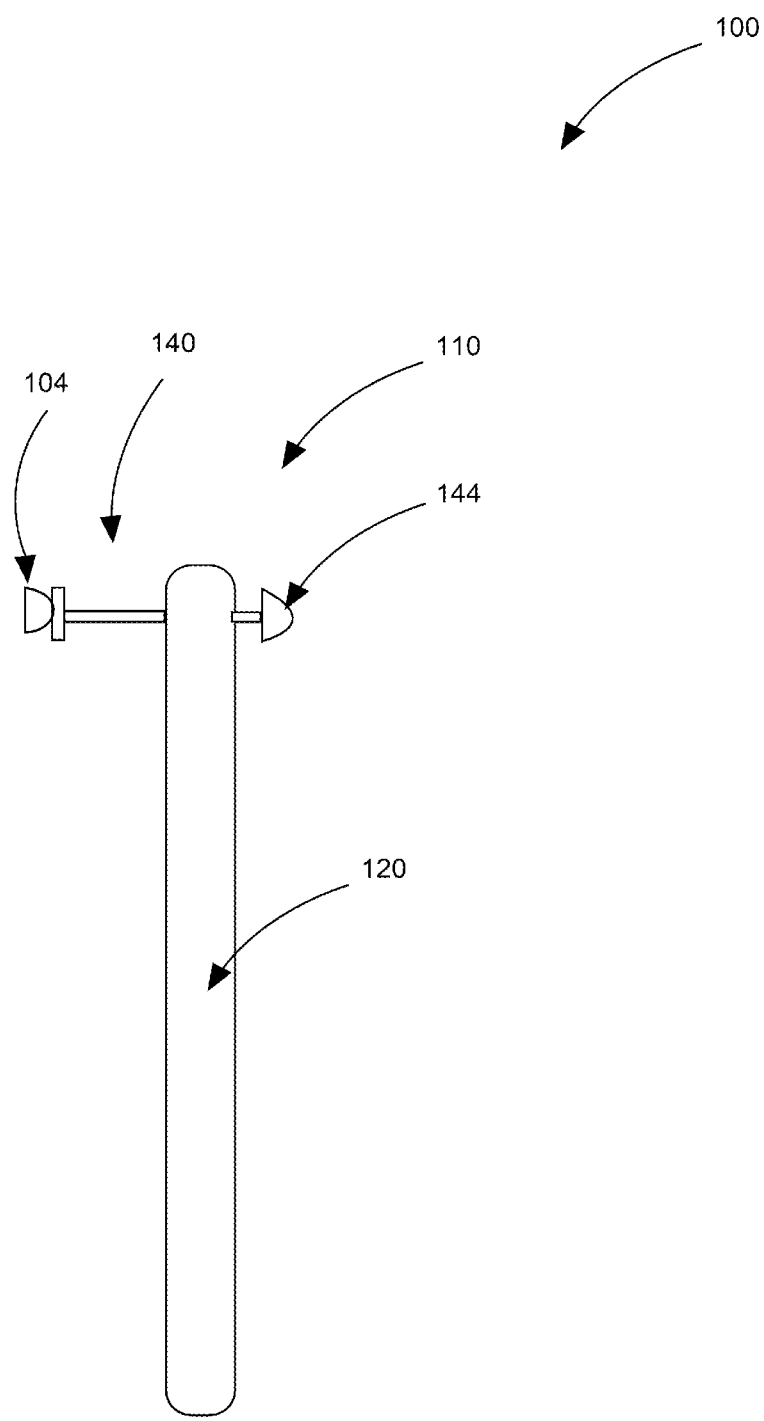
FIG. 4 is another perspective view illustrating the handheld contact applicator assembly according to an embodiment of the present invention of FIG. 1.

Referring now to FIGS. 3-4, perspective views illustrating handheld contact applicator assembly 110 according to an embodiment of the present invention of FIG. 1.

Contact engager 146 of handheld contact applicator system 100 is preferably somewhat flexible; not rigid but semi-rigid to avoid potential eye injury. As shown in FIG. 1 contact engager 146 is normally concave-tensioned; wherein contact engager 146 engages contact lens 104 via capillary action (surface tension means) for the insertion as shown in FIG. 1. Contact engager 146 disengages contact lens 104 via breaking capillary action (surface tensioning) for the removal as shown in FIG. 2. Contact engager 146 is able to flex from a state of being the normally concave-tensioned to a convexed-position as shown in FIGS. 1-2, respectively. Those with ordinary skill in the art will now appreciate that upon reading this specification and by their understanding the art of adhering contact lens(es) as described herein, methods of attachment and detachment will be understood by those knowledgeable in such art.

Handheld contact applicator assembly 110 preferably comprises rubber, plastic or other suitably equivalent material. The present invention, as such, lends itself to cost-effective manufacturing; thus is desirable. When plastic is used it is soft in nature. Upon reading this specification, it should be appreciated that, under appropriate circumstances, considering such issues as user preferences, design preference, structural requirements, marketing preferences, cost, available materials, technological advances, etc., other materials such as, for example, various forms of plastics, rubbers, rubberized materials, composites, non-plastics, etc., may be sufficient.

Relationally speaking inserter/remover assembly 140 is nearest proximate end 122 of handle body 120. Handheld contact applicator assembly 110 is able to be used as a hygienic means of adjusting the contact lens 104 which may have slipped off a cornea (in addition to insertion and removal means.) When referring herein to contact lens 104; contact lens 104 may comprise a soft-lens; a hard-lens; a gas-permeable-lens; and/or an extended-wear-lens. The present invention is multi-functional in use with a variety of contact lens 104.

Handheld contact applicator system 100 may be sold as kit with sets of contact lens 104; and also comprise at least one set of user instructions. The kit has instructions such that functional relationships are detailed in relation to the structure of the invention (such that the invention can be used, maintained, or the like in a preferred manner). Handheld contact applicator system 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different inserting/removing means and combinations, parts may be sold separately, etc., may be sufficient.

Figure 5:
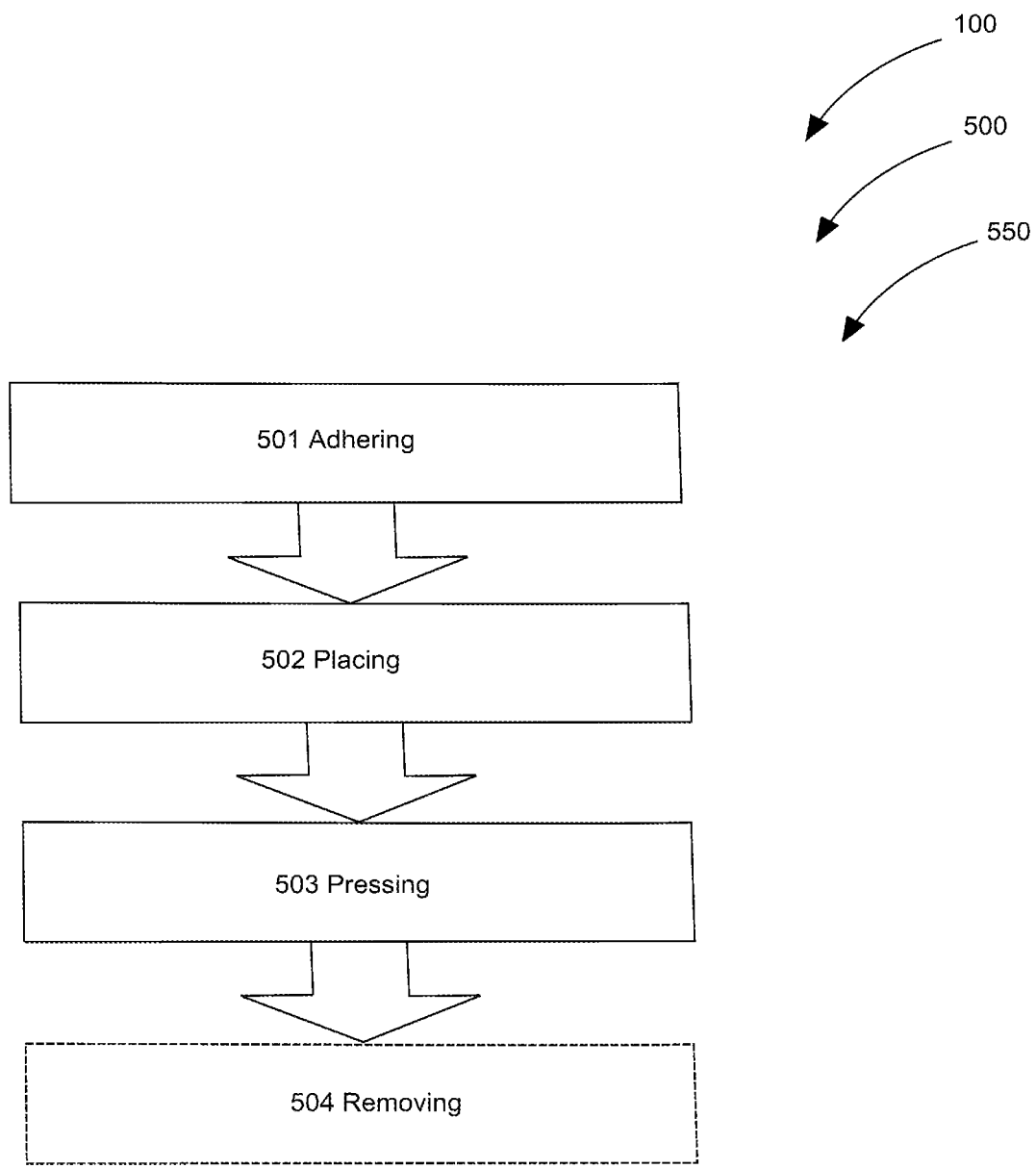
FIG. 5 is a flowchart illustrating a method of use for the handheld contact applicator system according to an embodiment of the present invention of FIGS. 1-4.

Referring now to FIG. 5, a flowchart 550 illustrating a method of use 500 for handheld contact applicator system 100 according to an embodiment of the present invention of FIGS. 1-4.

A method of using (method of use 500) handheld contact applicator system 100 may comprise the steps of: step one 501 adhering contact lens 104 to contact engager 146 of handheld contact applicator assembly 110 (via surface tension—using liquid or the like), step two 502 placing contact lens 104 onto an eye surface, and step three 503 pressing release button 144 to release contact lens 104 and couple contact lens 104 onto the eye surface for wear. Thus remote insertion may occur without direct use of a finger. The method 500 may further comprise the step four 504 of removing contact lens 104 from the eye surface when wearing is completed, also without direct use of at least one finger adjacent the eye surface.

It should be noted that step 504 is an optional step and may not be implemented in all cases. Optional steps of method 500 are illustrated using dotted lines in FIG. 5 so as to distinguish them from the other steps of method 500.

It should be noted that the steps described in the method of use can be carried out in many different orders according to user preference. The use of "step of" should not be interpreted as "step for", in the claims herein and is not intended to invoke the provisions of 35 U.S.C. §112, ¶ 6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A handheld contact applicator system comprising:
   a handheld contact applicator assembly having;
      a handle body having;
         a proximate end;
         a distal end;
         an aperture; and
         a length;
      an inserter/remover assembly having;
         a shaft;
         a release button; and
         a contact engager;
   wherein said handheld contact applicator system comprises said handheld contact applicator assembly;
   wherein said handheld contact applicator assembly comprises said handle body and said inserter/remover assembly in cooperative and functional combination;
   wherein said handle body comprises said proximate end, said distal end, said aperture, and said length;
   wherein parameters of said handle body are defined by said proximate end, and said distal end having said length thereby defined;
   wherein said aperture passes through said handle body;
   wherein said inserter/remover assembly comprises said shaft, said release button, and said contact engager;
   wherein said inserter/remover assembly is in mechanical communication with said handle body, said shaft passing through said aperture perpendicular to said handle body, said release button located on a terminal end of said shaft and said contact engager located opposing said release button on a leading end of said shaft;
   wherein said release button is manually activated when depressed, to facilitate release for insertion and alternately to couple to for removal, a contact lens touch-coupled to said contact engager; and
   wherein said handheld contact applicator assembly is structured and arranged to facilitate insertion and removal of said contact lens in a remote capacity in order to effectively eliminate finger to eye contact;
   wherein said shaft comprises a tubular rod which is semi-rigid.

2. The handheld contact applicator system of claim 1 wherein said contact engager is flexible.

3. The handheld contact applicator system of claim 1 wherein said contact engager is normally concave-tensioned.

4. The handheld contact applicator system of claim 3 wherein said contact engager is able to flex from a state of being said normally concave-tensioned to a convexed-position.

5. The handheld contact applicator system of claim 1 wherein said contact engager engages said contact lens via surface tension for said insertion.

6. The handheld contact applicator system of claim 1 wherein said contact engager disengages said contact lens via breaking surface tension for said removal.

7. The handheld contact applicator system of claim 1 wherein said handheld contact applicator assembly comprises plastic.

8. The handheld contact applicator system of claim 7 wherein said plastic is soft.

9. The handheld contact applicator system of claim 1 wherein said inserter/remover assembly is nearest said proximate end of said handle body.

10. The handheld contact applicator system of claim 1 wherein said handheld contact applicator assembly is able to be used as a hygienic means of adjusting said contact lens which have slipped off a cornea.

11. The handheld contact applicator system of claim 1 wherein said contact lens comprises a soft-lens.

12. The handheld contact applicator system of claim 1 wherein said contact lens comprises a hard-lens.

13. The handheld contact applicator system of claim 1 wherein said contact lens comprises a gas-permeable-lens.

14. The handheld contact applicator system of claim 1 wherein said contact lens comprises an extended-wear-lens.

15. The handheld contact applicator system of claim 1 wherein said release button is spring-tensioned.

* * * * *